US011166638B2

(12) United States Patent
Choudhary et al.

(10) Patent No.: US 11,166,638 B2
(45) Date of Patent: Nov. 9, 2021

(54) DEVICE FOR MEASURING PRESSURE PULSES BASED ON APPLANATION TONOMETRY

(71) Applicants: INDIAN INSTITUTE OF TECHNOLOGY DELHI, Delhi (IN); ALL INDIA INSTITUTE OF MEDICAL SCIENCES, Delhi (IN)

(72) Inventors: Ikbal M. Choudhary, Delhi (IN); Rajnish Juneja, Delhi (IN); Anamika Prasad, Delhi (IN); Sitikantha Roy, Delhi (IN)

(73) Assignee: INDIAN INSTITUTE OF TECHNOLOGY DELHI, Delhi (IN)

( * ) Notice: Subject to any disclaimer, the term of this patent is extended or adjusted under 35 U.S.C. 154(b) by 137 days.

(21) Appl. No.: 16/325,975

(22) PCT Filed: Aug. 16, 2017

(86) PCT No.: PCT/IN2017/050349
§ 371 (c)(1),
(2) Date: Feb. 15, 2019

(87) PCT Pub. No.: WO2018/033938
PCT Pub. Date: Feb. 22, 2018

(65) Prior Publication Data
US 2019/0183351 A1 Jun. 20, 2019

(30) Foreign Application Priority Data
Aug. 16, 2016 (IN) .............................. 201611027931

(51) Int. Cl.
*A61B 5/022* (2006.01)
*A61B 5/00* (2006.01)
*A61B 5/021* (2006.01)

(52) U.S. Cl.
CPC ................ *A61B 5/022* (2013.01); *A61B 5/00* (2013.01); *A61B 5/021* (2013.01); *A61B 5/681* (2013.01); *A61B 5/6824* (2013.01); *A61B 5/6831* (2013.01)

(58) Field of Classification Search
CPC ............ A61B 5/02416; A61B 5/02255; A61B 5/6843; A61B 5/681; A61B 5/6824; A61B 5/022; A61B 5/00; A61B 5/021; A61B 5/6831
See application file for complete search history.

(56) References Cited

U.S. PATENT DOCUMENTS

2002/0177781 A1 11/2002 Amano
2005/0177047 A1* 8/2005 Harpas ................... A61B 5/489
600/485

(Continued)

FOREIGN PATENT DOCUMENTS

WO 2016040256 3/2016

OTHER PUBLICATIONS

Joshua Rose (Modern Machine-Shop Practice, vols. I and II, copyright 1887, p. 120, Figure 417) (hereinafter—Rose) (Year: 1887).*

(Continued)

*Primary Examiner* — Devin B Henson
*Assistant Examiner* — Justin Xu
(74) *Attorney, Agent, or Firm* — Meunier Carlin & Curfman LLC

(57) ABSTRACT

The present invention relates generally to a non-invasive device for monitoring blood pressure using principle of applanation tonometry. A novel device for measuring pressure pulse comprises a differential screw mechanism, a sensor module connected to the screw mechanism, and an overall enclosure housing the sensor module and the differential screw mechanism in one unit. A pair of straps is attached to the enclosure, wherein said straps as a flex lock brace through a hinge to change the angle of extension of the (Continued)

wrist as required. The multi component sensor module comprises of a snap-fit enclosure, which houses a tactile-based force sensitive resistor, and a mechanism to transmit the forces from the artery. The force transmission mechanism comprises of a gel layer and a gel head. The differential screw mechanism ensures precise hold down pressure in multiple stages via screwing and unscrewing steps to accurately measure the blood pressure.

10 Claims, 9 Drawing Sheets

(56) References Cited

U.S. PATENT DOCUMENTS

2009/0131806 A1* 5/2009 Finburgh ............... A61B 5/022
600/485
2012/0059298 A1* 3/2012 Hoffman ............ A61N 1/36003
602/21
2017/0086686 A1* 3/2017 Narasimhan ....... A61B 5/02444
2017/0332919 A1* 11/2017 Eagle ................. A61B 5/02007

OTHER PUBLICATIONS

"Snap Fit Design" (Behrend College, Pennsylvania State University (Erie, Pennsylvania, USA), 2003 https://web.archive.org/web/20070102180708/http://engr.bd.psu.edu/pkoch/plasticdesign/snap_design.htm ) (hereinafter—Behrend College) (Year: 2003).*
International Search Report and Written Opinion dated Oct. 27, 2017, from International Application No. PCT/IN2017/050349, 7 pages.

* cited by examiner

DEVICE FOR MEASURING PRESSURE PULSES BASED ON APPLANATION TONOMETRY

RELATED APPLICATION

This application claims priority under section 9(1) to IN Provisional Application No. 201611027931, filed Aug. 16, 2016 and titled "A NOVEL DEVICE FOR MEASURING PRESSURE PULSES BASED ON APPLANATION TONOMETRY," which is hereby incorporated by reference in its entirety.

FIELD OF THE INVENTION

This invention relates generally to a non-invasive device for monitoring blood pressure using applanation tonometry, and more particularly, this invention elaborates on a mechanism to acquire the pressure waveforms using an off-the-shelf tactile-based force sensor.

BACKGROUND OF THE INVENTION

Methods for accurately monitoring the blood pressure waveform have been under investigation for some time. While invasive methods can provide accurate waveforms, the trauma caused to a patient makes such techniques undesirable in many cases. One such method involves the use of a fluid filled catheter inserted into a patient's artery. While accurate blood pressure measurements can be obtained by this method, the negative effects on the patient often outweigh the benefits of achieving accurate results from such a method.

Routine methods of monitoring a patient's blood pressure waveform include the widely used auscultatory method known as the Korotkoff method. This method is non-invasive, however, it only provides a measurement of systolic and diastolic pressure on an intermittent basis, and it does not provide the entire waveform on a continuous basis. Furthermore, use of the Korotkoff method often yields inaccurate results. Moreover, the rate at which blood pressure can be recorded is limited by the inflation and deflation rate of the occlusive cuff. Therefore, true beat to beat continuous blood pressure monitoring is not possible using this method.

Further, Tonometric blood pressure measurement is a non-invasive means for continuously monitoring blood pressure. The technique uses the principle of applanation tonometry for acquiring pressure pulse from a peripheral artery. Under operating conditions, arterial tonometry can faithfully give the right pulse waveforms that can be calibrated to a blood pressure. Quite a number of products have come up in the market with varying degrees of accuracy and use case. This is because the focus now has started to shift from discreet two-value BP readings to pulse waveforms, as the latter is more representative of a number of hemodynamic and physiological parameters and overall cardiovascular health.

However most of the available devices are cuff-based, expensive and used only in clinical settings for the purpose of research. Additionally due to factors such as wrist shape, size and position of the artery below the skin, a general plunger/transducer of the non-invasive device may not be able to compress the artery to the desired point. Therefore, there is a need for a simple, affordable, cuffless and non-invasive device to get blood pressure waveforms both in clinical and home settings.

OBJECTIVE OF THE INVENTION

These objectives are provided to introduce a selection of concepts in a simplified form that are further described below in the detailed description. These objectives are not intended to identify key features or essential features of the claimed subject matter, nor is it intended to be used as an aid in determining the scope of the claimed subject matter.

An important objective of the invention aims at providing a compact solution for the shortcomings of the above mentioned systems.

Another objective of the invention is to provide a device, which overcomes the shortcomings of existing tonometric devices.

Yet another objective of the invention is to provide a modular device, which is adapted to serve more than one purpose and use case apart from calculating the blood pressure.

A further objective of the current invention is to provide a robust mechanism to acquire the pressure pulse waveforms using an off-the-shelf tactile based force sensor which thereby may lead to a cost effective process thereof.

Another objective of the present invention is to provide specific design features on the sensor module which minimizes the stress concentration due to compression of the skin over and away from the artery.

These objectives are achieved by the device according to the invention, which is a novel device for measuring pressure pulses, comprising a differential screw mechanism, a sensor module connected to the screw mechanism, and an overall enclosure housing the sensor module and the differential screw mechanism in one unit. A pair of straps is attached to the enclosure, wherein said straps act as a flex lock brace through a hinge to change the angle of extension of the wrist as required. The multi component sensor module comprises of a snap-fit enclosure, which houses a tactile-based force sensitive resistor (FSR), and a mechanism to transmit the forces from the artery. The force transmission mechanism comprises of a gel layer and a gel head. The differential screw mechanism ensures precise hold down pressure in multiple stages via screwing and unscrewing steps to accurately measure the blood pressure.

BRIEF DESCRIPTION OF THE DRAWINGS

The above and other aspects, features, and advantages of certain exemplary embodiments of the present invention will be more apparent from the following description taken in conjunction with the accompanying drawings in which:

FIG. 8a is a graphical representation of a contact pressure along the line of contact of the sensor module on the skin plotted as a function of distance from artery axis, and 8b represents a 2D computational model of the wrist and sensor module;

Figure 1:
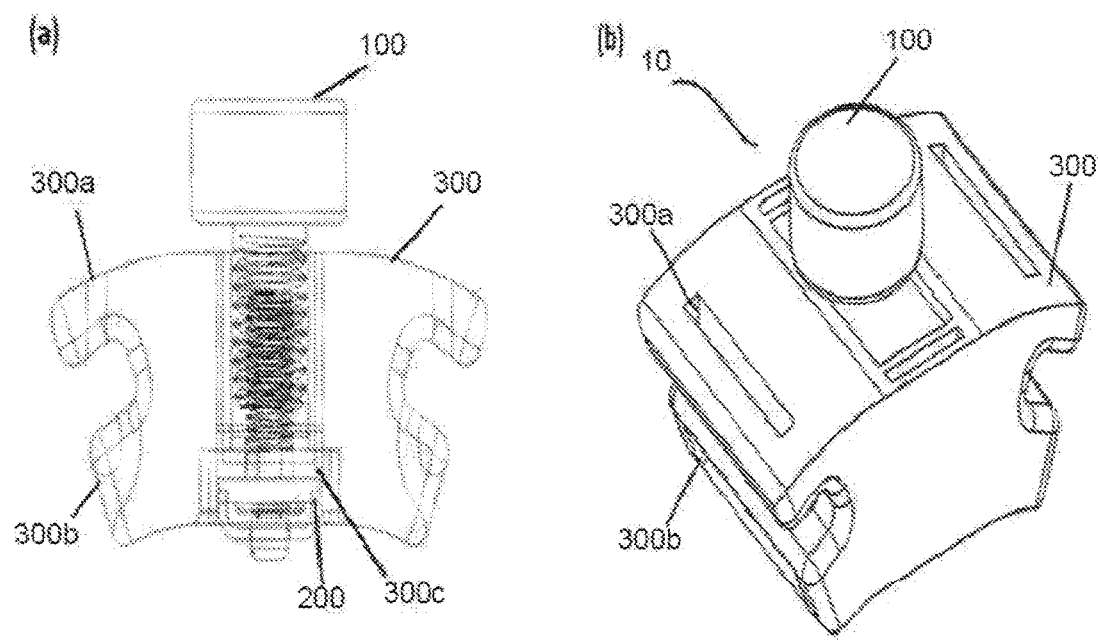
FIGS. 1a and 1b are diagrammatic schematic representations of an assembly of the device, according to an embodiment of the present invention.

Persons skilled in the art will appreciate that elements in the figures are illustrated for simplicity and clarity and may have not been drawn to scale. For example, the dimensions of some of the elements in the figure may be exaggerated relative to other elements to help to improve understanding of various exemplary embodiments of the present disclosure.

Throughout the drawings, it should be noted that like reference numbers are used to depict the same or similar elements, features, and structures.

DETAILED DESCRIPTION OF THE INVENTION

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. In addition, descriptions of well-known functions and constructions are omitted for clarity and conciseness.

In the claims, all transitional phrases such as "comprising," "including," "carrying," "having," "containing," "involving," and the like are to be understood to be open-ended, i.e., to mean including but not limited to. Only the transitional phrases "consisting of and "consisting essentially of," respectively, shall be closed or semi-closed transitional phrases.

To facilitate the understanding of this invention, a number of terms may be defined below. Terms defined herein have meanings as commonly understood by a person of ordinary skill in the areas relevant to the present invention. Terms such as "a", "an", and "the" are not intended to refer to only a singular entity, but include the general class of which a specific example may be used for illustration. The terminology herein is used to describe specific embodiments of the invention, but their usage does not delimit the disclosed system or method, except as may be outlined in the claims.

The details of the various elements of a novel modular device for acquiring pressure pulses from a superficial artery using applanation tonometry will now be described in order to enable those skilled in the art to practice this invention.

FIGS. 1a and 1b are diagrammatic schematic representations of assembly of the device, according to an embodiment of the present invention. Accordingly a novel device 10 for measuring pressure pulses consists of a differential screw mechanism 100, a sensor module 200, and an enclosure 300. Where, the differential screw mechanism 100 and the sensor module 200 are connected and the unit is accommodated by an enclosure 300. The enclosure 300 is a solid block which houses differential screw mechanism 100. The ends of the enclosure 300 have flanges with holes 300a and 300b for fixing of straps 302, and hole 300c at the bottom of enclosure 300 for positioning of sensor module 200.

Figure 2:
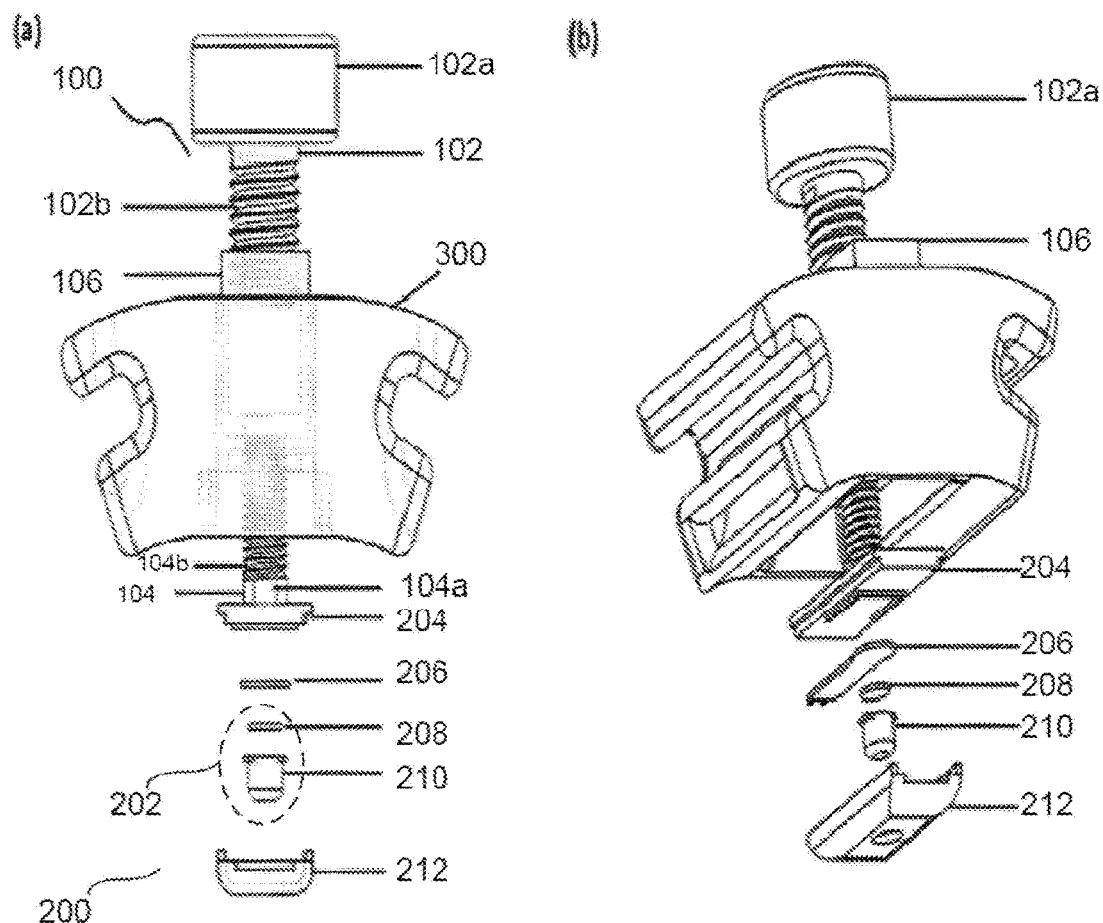
FIGS. 2a and 2b are diagrammatic schematic representations of an exploded view of the components in the device, according to an embodiment of the present invention.
Figure 3:
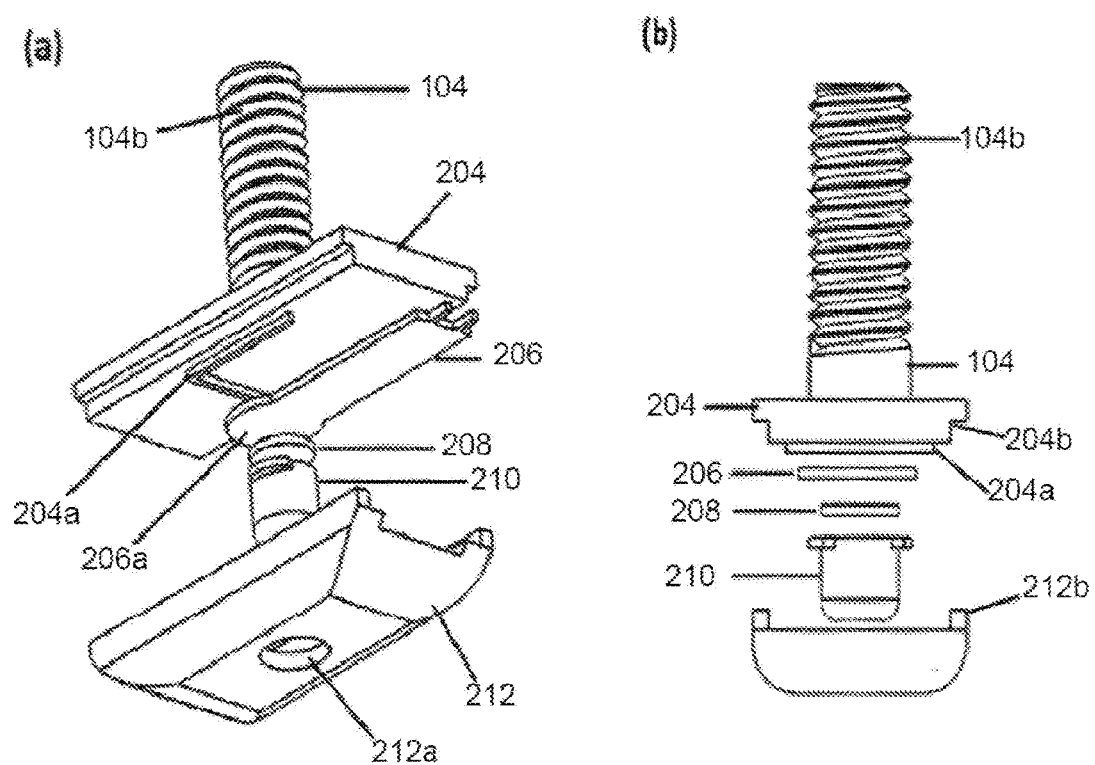
FIGS. 3a and 3b are diagrammatic schematic representations of an exploded view of the components of sensor module, according to an embodiment of the present invention.

FIGS. 2a and 2b are diagrammatic schematic representations of exploded view of the components in the device, according to an embodiment of the present invention. The differential screw mechanism 100 comprises of a large bolt 102 with a bolt head also called as knob 102a, a small bolt 104 and a block 106. The block 106 has inner screw threads and it houses the large bolt 102 and the small bolt 104 together. Further the small bolt has a key 104a at the bottom. In an embodiment, the larger bolt 102 has 10 mm diameter having outer thread profile 102b with pitch of 1.5 mm. Similarly the small bolt 104 has 6 mm diameter having outer thread profile 104b with pitch of 1 mm. The circular motion of the knob 102a causes the small bolt 104 to translate in the vertical direction, depending on the effective pitch. The sensor module 200 connected to the small bolt 104 of the differential screw mechanism 100, comprises of a two-part snap-fit enclosure with a bottom plate 204 and a top plate 212 which houses a sensor 206 and a force transmission mechanism 202. The bottom plate 204 of the sensor module 200 has protruded guide way 204a to ensure the active area 206a of the sensor 206 remains in line with the force transmission mechanism 202 and a circular opening 212a in the top plate of the sensor module 212. The top plate 212 has rectangular grooves 212b on it. The bottom plate 204 has rectangular slots 204b in it to enable a snap-fit assembly. The device uses one or more, rigid or flexible off-the-shelf force sensors 206 belonging to the broad class of tactile-based force sensitive-resistor (FSR). The corresponding diagrammatic schematic representation of exploded view of the components of sensor module, according to an embodiment of the present invention is shown in FIGS. 3a and 3b.

Figure 4:
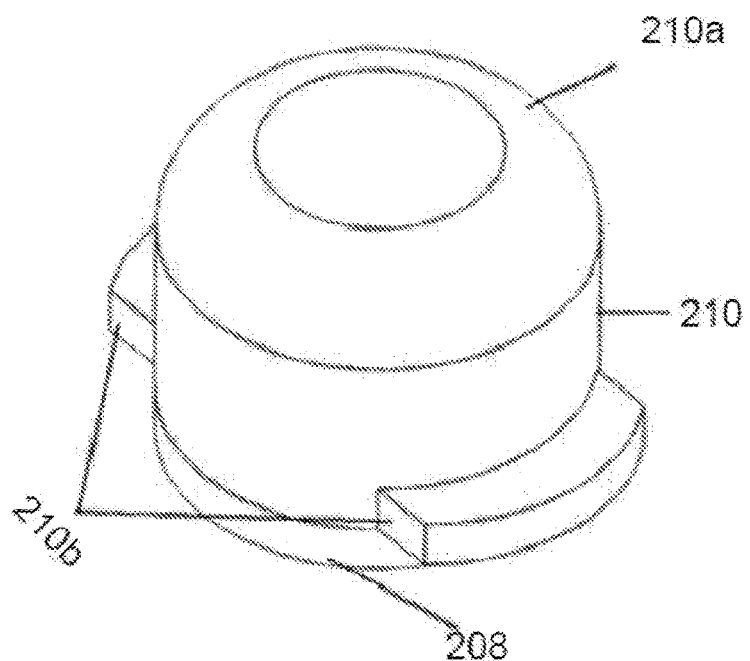
FIG. 4 is diagrammatic schematic representation of an assembly of force transmission mechanism, according to an embodiment of the present invention.

FIG. 4 is a diagrammatic schematic representation of an assembly of a force transmission mechanism, according to an embodiment of the present invention. The force transmission mechanism 202 consists of a gel-head 210, also called an arterial rider, and a gel-layer 208, also known as a spring element, which makes one single spring-mass unit. The gel head is in tubular shape having a top flat end and a flat bottom end. The periphery of the top end has design feature 210a to relieve stress concentration and the bottom of gel head 210 has plurality of flanges 210b for firmly placing gel head 210 through hole 212a of the top plate 212 to ensure gel head remains in the sensor module 200. The gel-head 210 is stiffer and heavier than the gel-layer 208, in order to faithfully capture the blood pressure waveform. The gel-layer 208 protects the sensor 206 from mechanical damage apart from providing a spring action to the gel-head 210. The gel-layer 208 may be made up of elastomers like silicone, polyurethane, etc. The design feature 210a reduces the stress concentration along the periphery of the gel-head 210.

Figure 5:
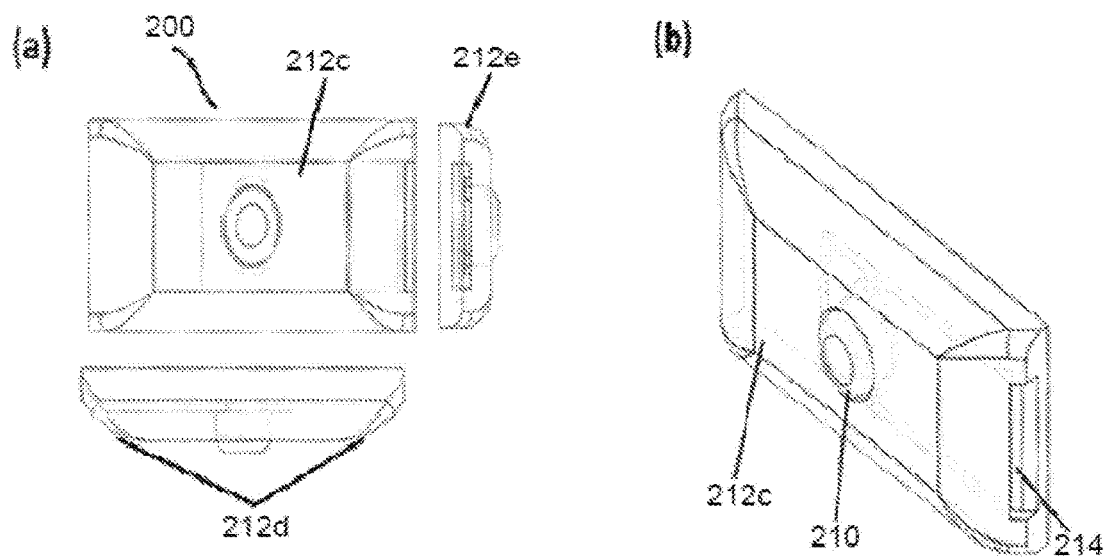
FIGS. 5a and 5b are diagrammatic schematic representations of a top, side and isometric views of the assembly of single sensor module, according to an embodiment of the present invention.

FIGS. 5a and 5b are diagrammatic schematic representations of top, side and isometric view of the assembly of sensor module according to an embodiment of the present invention. A sensor module 200 has a flat base 212c on the top plate 212 which presses the skin on top of the artery. The top plate 212 having a flat base 212c with an opening 212a, connected to sides through plurality of design features 212d and 212e to reduce stresses on edges. The design feature 212d along the side's enables smooth transition of the artery while under compression. Other design feature 212e reduces the stresses developed on the edges of the module. Further, the sensor module 200 also has an opening slot 214 to enable connection between the sensor 206 and plurality of wires. The sensor module 200 can be a single or multi sensor module. In a multi sensor module assembly of one or more sensors, gel-heads, gel-layers can be accommodated in the module based on the use case.

The plurality of design features 212d and 212e in the sensor module assists the active area of the sensor to pick up the pressure from the flat surface of the compressed artery without accumulation of unnecessary bending stresses and further lowers disturbances like micro turbulences in the blood flow in the artery so the blood flow remains laminar in the measurement area. Furthermore, the design of the module ensures minimal stress concentration due to compression of the skin over and away from the artery i.e. the stresses developed at the boundary of the flattening mechanism don't influence the forces measured by the sensor on the artery. The pressure pulses are acquired from the center of the module using a force transmission mechanism as described earlier. This feature ensures that the device measures only the forces due to the blood pressure and not stresses from the adjoining tissues.

Figure 6:
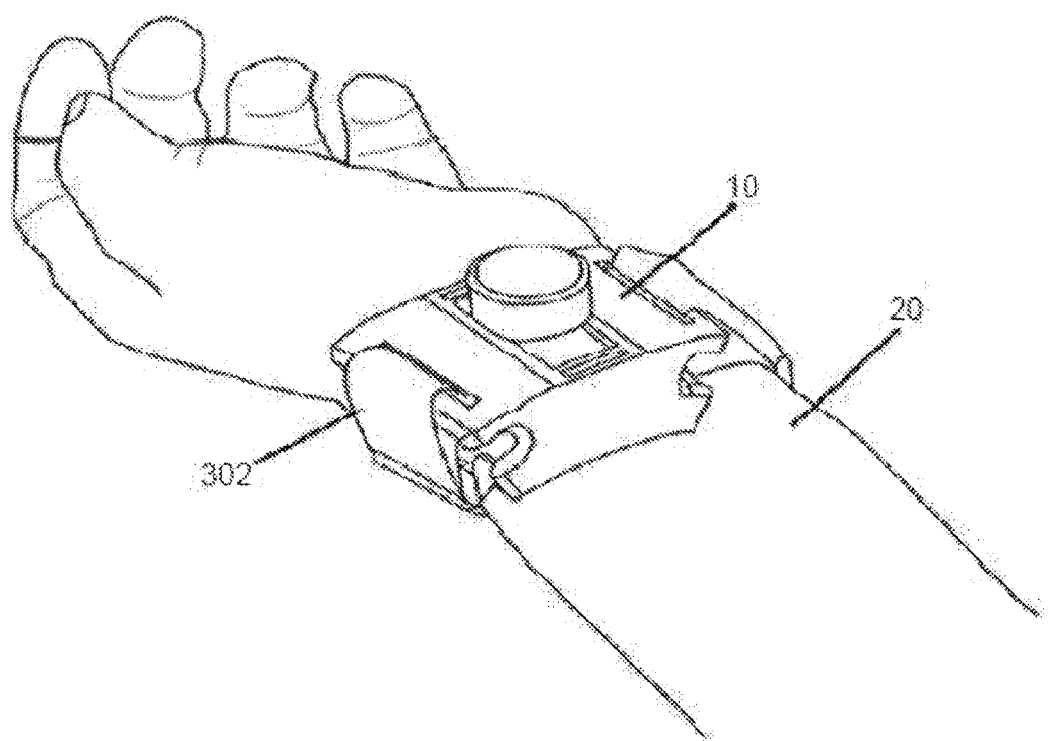
FIG. 6 is a diagrammatic representation of the device on the wrist, according to an embodiment of the invention.
Figure 7:
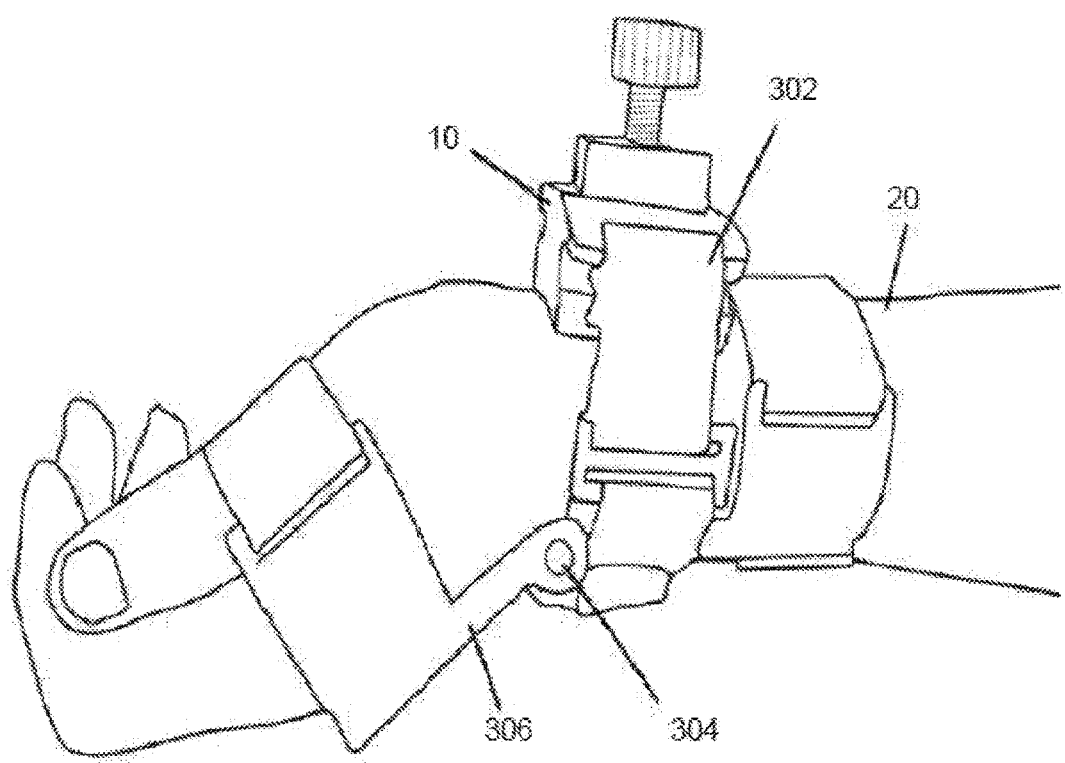
FIG. 7 is a diagrammatic representation of a side view of the device with the flex-lock brace, according to an embodiment of the invention.

FIG. 6 is a diagrammatic representation of the device on wrist, according to an embodiment of the invention. The enclosure of the blood pressure measuring device 10 is attached with a pair of straps 302 to wear the device 10 on wrist 20. Further the straps 302 supports a flex-lock brace 306 through a hinge 304. The flex-lock brace 306 can be rotated about a hinge 304 to change the angle of extension of the wrist 20 as required. The corresponding FIG. 7 shows diagrammatic representation of side view of the device along with the flex-lock brace.

FIG. 8a is a graphical representation of a contact pressure along the line of contact of the sensor module on the skin plotted as a function of distance from artery axis, according to an embodiment of the invention. from the graph the two stress peaks on the two ends of the module is due to compression of the skin. However due to design feature 212e in the sensor module, the stresses don't interfere with the force transmission along the center of the artery. A uniform pressure of 100 mmHg was applied in the artery, and therefore after compressing the artery to the right extent, the pressure at the center of the gel-head is 100 mmHg. The two small peaks near the center line indicate the stresses due to bending of the artery. FIG. 8b represents a 2D computational model of the wrist and sensor module developed for the study.

Figures 8, 9:
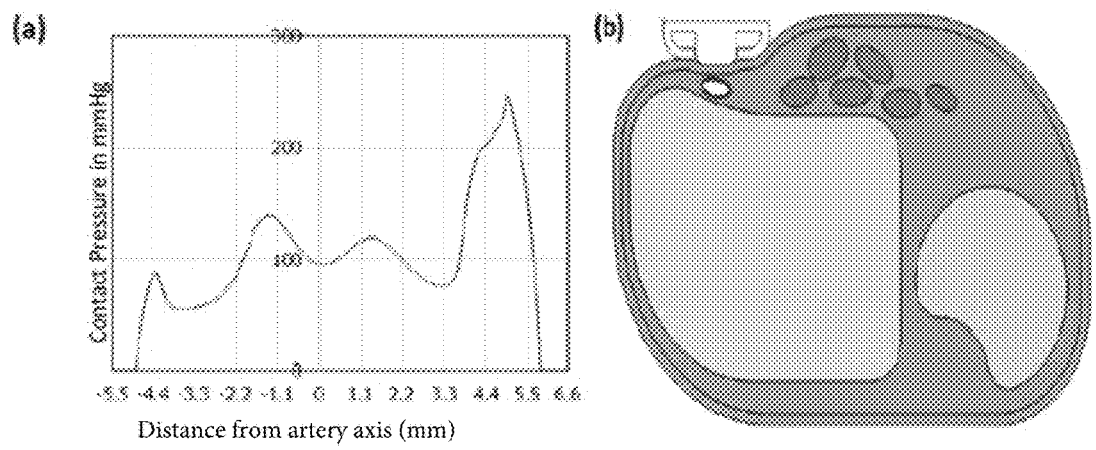
FIG. 9 is a graphical representation of pressure versus time plot data acquired using the device using a low-pass filter and a high pass filter.

FIG. 9 is a graphical representation of pressure versus time plot of the data acquired using the device via step-wise compression and release of the artery using the differential screw. The sensor picks up both the pressure due to the BP in the artery ($DC_1$+AC component) and also the stress due to compression of the skin and artery in definite screw steps ($DC_2$ component). Further the black colored plot corresponds to the ($DC_1$+AC) and $DC_2$ components. On using a bandpass filter of cut-off 0.3-5 Hz, the signal can be filtered down to have only AC signal as shown as the grey plot in FIG. 9.

Figure 10:
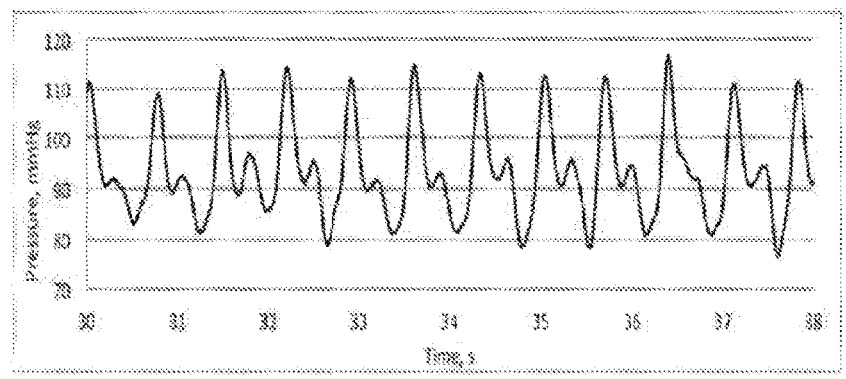
FIG. 10 is a graphical representation of a pressure and time plot of the calibrated pulse waveforms.

FIG. 10 is a graphical representation of pressure and time plot of the pulse waveforms calibrated to BP. The BP can be calculated by calibrating the AC plot of FIG. 9 using mean arterial pressure ($P_{MAP}$) obtained separately via a standard cuff-based measurement. However, the pulse pressure waveforms can be acquired from FIG. 9 without BP calibration.

Figure 11:
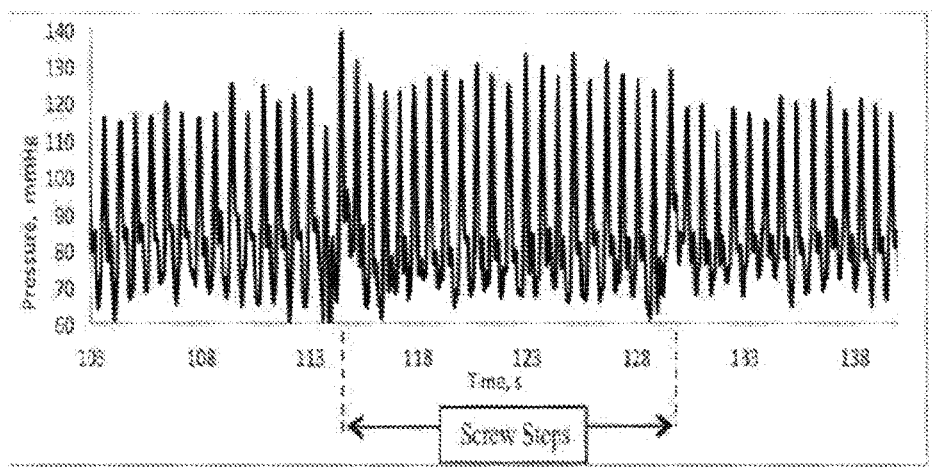
FIG. 11 is a graphical representation of a pressure and time plot with steps demarcation.

FIG. 11 is a graphical representation of pressure and time plot with steps demarcation. The steps are defined by rotating the knob 102a of the larger bolt 102 while taking the readings. Each step corresponds to a screw rotation of 180°, which makes the sensor module move downwards or upwards by 0.25 mm. The downward and upward movement depends on whether the knob 102a was rotated anticlockwise or clockwise.

Another embodiment of the present invention is the use of differential screw mechanism 100 in the device 10. The screw mechanism 100 has an effective pitch of 0.5 mm and is connected to the flat base of the multi-component sensor module 200. The differential screw mechanism 100 enables the sensor module 200 to manually flatten the artery in multiple steps with precise control as shown in FIG. 9. Ideally blood pressure waveforms should be noted when the pulse amplitude is maximum. However mechanically achieving and maintaining this state is very difficult. In that context the differential screw mechanism 100 is very useful as it is capable of moving the sensor module 200 up or down by sub-millimeter steps. Therefore differential screw mechanism 100 helps the sensor module 200 acquire pressure pulses when the pulse amplitude is maximum.

Further differential screw mechanism 100 enables the device to reach the location where the artery is sufficiently flattened so that the bending stresses developed at the edges of the artery are perpendicular to direction of force transmission from artery to the sensor. If the artery is not sufficiently flattened, the bending stresses developed at the periphery of the artery will influence the blood pressure measurement at the center of the artery.

Since it is a differential screw 100, the upward and downward movement of the module 200 can be precisely controlled. This ensures that we get the right waveform with maximum pulse amplitude when the bending stresses are minimal.

In yet another embodiment, the present invention identifies an enclosure 300 which houses both the differential screw mechanism 100 and the multi-component sensor module 200 shown in FIG. 1. The enclosure 300 along with the straps 302 maintains stability of data acquisition. This mechanism is robust and repeatable for acquiring pressure pulses. The fabrication and assembly of the components are much cheaper than the existing devices for capturing and storing data. Also the device can be worn on the wrist as shown in FIG. 6 and FIG. 7 and various protocols can be easily followed to conduct physiological tests.

While the preferred embodiment of the invention has been illustrated and described herein, it is to be understood that the invention is not limited to the precise construction herein disclosed, and the right is reserved to all changes and modifications coming within the scope of the invention.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The invention claimed is:

1. A non-invasive device for measuring pressure pulses, comprising:
   a differential screw mechanism, a sensor module connected to the differential screw mechanism, and an enclosure accommodating the sensor module and the differential screw mechanism in one unit, wherein:

the differential screw mechanism comprises a large bolt with a bolt head, a small bolt, and a block, the block having inner screw threads coupling the large bolt and the small bolt such that rotational motion of the bolt head about a longitudinal axis of the large bolt enables the small bolt to translate in an axial direction, wherein the small bolt has first and second ends, and the first and second ends are axially spaced apart from the bolt head in one axial direction; and the sensor module comprises a sensor, a force transmission mechanism, and a snap-fit casing having a bottom plate and a top plate for housing the sensor and the force transmission mechanism, wherein the force transmission mechanism has a gel-head and a gel-layer arranged inline along the axis for capturing blood pressure waveforms for measuring pressure pulses, wherein the gel layer is disposed between the sensor and the gel head and the gel layer directly abuts the sensor; and a pair of straps attached to the enclosure, wherein the straps support a flex-lock brace through a hinge, to change an angle of extension of a wrist.

2. The non-invasive device for measuring pressure pulses according to claim 1, wherein the differential screw mechanism controls the upward and downward movement of the sensor module.

3. The non-invasive device for measuring pressure pulses according to claim 1, wherein the larger bolt and smaller bolt in the differential screw mechanism has different pitch to control the flattening of an artery in precise steps.

4. The non-invasive device for measuring pressure pulses according to claim 1, wherein the snap fit is formed between the rectangular grooves of the top plate and rectangular slots of the bottom plate.

5. The non-invasive device for measuring pressure pulses according to claim 1, wherein the bottom plate has a protruded guide way to align the sensor in line with the force transmission mechanism.

6. The non-invasive device for measuring pressure pulses according to claim 1, wherein the sensor is an off-the-shelf tactile based force sensor.

7. The non-invasive device for measuring pressure pulses according to claim 1, wherein the gel-layer is made of elastomer.

8. The non-invasive device for measuring pressure pulses according to claim 1, wherein the top plate has a flat base defining a hole, the top plate being connected to a plurality of side walls and wherein the plurality of side walls comprises a plurality of design features that abut the plurality of side walls to reduce stresses on edges of the plurality of side walls.

9. The non-invasive device for measuring pressure pulses according to claim 1, wherein the gel head has a tubular shape having a top flat end and a flat bottom end, wherein a top end periphery of the gel-head has a design feature to relieve stress concentration and the bottom of the gel head has a plurality of flanges for firmly placing the gel head through the top plate.

10. The non-invasive device for measuring pressure pulses according to claim 1, wherein at least one of the plurality of side walls of the sensor module has an opening to enable connection between the sensor and plurality of wires.

\* \* \* \* \*